United States Patent [19]

Molt

[11] 4,356,279
[45] Oct. 26, 1982

[54] 2,2,6,6-TETRAMETHYL-4-PIPERIDYL-SUBSTITUTED HETEROCYCLIC RING COMPOUND AND POLYMERS CONTAINING SAME

[75] Inventor: Kenneth R. Molt, Cincinnati, Ohio

[73] Assignee: Carstab Corporation, Reading, Ohio

[21] Appl. No.: 286,400

[22] Filed: Jul. 23, 1981

Related U.S. Application Data

[62] Division of Ser. No. 117,878, Feb. 4, 1980, abandoned.

[51] Int. Cl.³ .............................................. C08K 5/34
[52] U.S. Cl. .................................. 524/102; 524/105; 524/180; 524/291
[58] Field of Search ......................................... 524/102

[56] References Cited

U.S. PATENT DOCUMENTS

| | | | |
|---|---|---|---|
| 4,251,435 | 2/1981 | Son et al. | 546/17 |
| 4,279,804 | 7/1981 | Cantatore et al. | 546/186 |
| 4,293,467 | 10/1981 | Hardy et al. | 546/189 |

*Primary Examiner*—John Kight, III
*Assistant Examiner*—R. A. White
*Attorney, Agent, or Firm*—Richard J. Sheridan; Gerald K. White

[57] ABSTRACT

A novel 2,2,6,6-tetramethyl-4-piperidyl substituted nitrogen heterocyclic ring compound is provided which is useful as a stabilizer for organic polymers. Organic polymers containing the novel 2,2,6,6-tetramethyl-4-piperidyl substituted nitrogen heterocyclic ring compound exhibit improved resistance to deterioration induced by light, by heat or by a combination of light and heat. The novel 2,2,6,6-tetramethyl-4-piperidyl substituted nitrogen heterocyclic ring compound is prepared by a novel method comprising the step of reacting 2,2,6,6-tetramethyl-4-piperidyl substituted 1,2-aliphatic diamine with a monoaldehyde or dialdehyde.

7 Claims, No Drawings

2,2,6,6-TETRAMETHYL-4-PIPERIDYL-SUBSTITUTED HETEROCYCLIC RING COMPOUND AND POLYMERS CONTAINING SAME

This application is a division of application Ser. No. 117,878, filed Feb. 4, 1980, now abandoned.

This invention relates to novel 2,2,6,6-tetramethyl-4-piperidyl-substituted heterocyclic ring compounds, novel methods for their preparation and to stabilized polymer compositions containing these novel compounds. Further, this invention relates to methods for the stabilization of polymers wherein the novel 2,2,6,6-tetramethyl-4-piperidyl-substituted heterocyclic ring compound is added to the polymer.

BACKGROUND

That synthetic, and even many natural, organic polymers require stabilization against light, particularly ultraviolet light, and heat induced discoloration and deterioration of physical properties is well know. Organic polymers subjected to outdoor exposure often discolor and show a loss of physical properties as a result of the exposure to a combination of degradation inducing factors (e.g. ultraviolet light, heat, water and oxygen). Outdoor use of organic polymers not only subjects the polymers to the ultraviolet light of the sun but also the heat of the sun. This outdoor exposure to the ultraviolet light and heat of the sun takes place in the presence of oxygen in the air. Thus, there can exist various combinations of factors working to degrade the organic polymer. On the other hand there exist other uses of organic polymers which result in their exposure to heat and oxygen in the absence of ultraviolet light, or ultraviolet light and oxygen in the absence of heat or even heat in the absence of oxygen. Thus, many organic polymers require protection against deterioration induced by a variety of environmental conditions. Factors such as heat and oxygen are not only present during the commercial use of organic polymers but are also present during the processing of the polymer into finished articles of commerce. Stabilization of organic polymers against discoloration and loss of physical properties during processing into finished products is also required.

In view of the numerous applications and large scale use of organic polymers, it is very important to stabilize such organic polymers against the deteriorating effects of environmental factors during processing and use. To protect many organic polymers against undesirable changes in physical properties and discoloration during processing and use, various stabilizers and stabilizer combinations have been added to the organic polymers. Included among such stabilizers are, for example, the well known metal salts, organometallic compounds, phenols, hindered phenols, substituted and unsubstituted benzophenones, salicylates, mercaptans, expoxides and benzothiazoles. More recently hindered amine stabilizers having tetraalkyl substituted piperidino groups have been proposed as stabilizers. Although a large number of stabilizer compounds and stabilizer combinations, including the hindered amine type stabilizers have been proposed and some of them used, there continues the search for better stabilizers to overcome the deficiencies of known stabilizers. Among these deficiencies there are, for example, included low stabilizing efficiency, high cost, stabilizer instability, initial coloration of the polymer, volatility and odor. More effective, stable, easy to use and lower cost stabilizers are always sought.

It is, therefore, an object of this invention to provide a novel 2,2,6,6-tetramethyl-4-piperidyl substituted heterocyclic ring compound. Another object of this invention is to provide as highly effective stabilizer for organic polymers a 2,2,6,6-tetramethyl-4-piperidyl substituted heterocyclic ring compound. A further object of this invention is to provide highly stable organic polymer compositions comprising an organic polymer and a 2,2,6,6-tetramethyl-4-piperidyl substituted heterocyclic ring compound. It is a still further object of this invention to provide a method of stabilizing organic polymers comprising the step of adding to an organic polymer, normally susceptible to deterioration, a stabilizingly effective amount of a 2,2,6,6-tetramethyl-4-piperidyl substituted heterocyclic ring compound. An even further object is to provide a novel method for preparing the 2,2,6,6-tetramethyl-4-piperidyl substituted heterocyclic ring compounds of this invention.

SUMMARY OF INVENTION

The foregoing objects and others as will be apparent to those skilled in the art from the following description are now found to be achieved by the invention described herein. In accordance with this invention there is now provided (1) a novel compound having one to two bis(2,2,6,6-tetramethyl-4-piperidyl) substituted heterocyclic rings in which said heterocyclic ring has five ring atoms, two of which are non-adjacent nitrogen atoms and three of which are carbon atoms and having a 2,2,6,6-tetramethyl-4-piperidyl group bonded to each nitrogen atom of the heterocyclic ring (which compound for the sake of brevity shall hereinafter be called the hindered amine compound) and (2) a novel stabilized polymer composition comprising an organic polymer normally susceptible to light and/or heat induced degradation and the above described hindered amine compound according to this invention. Further, there is provided in accordance with this invention (1) a method of stabilizing an organic polymer normally susceptible to light and/or heat induced degradation comprising the step of adding to said polymer the above described hindered amine compound and (2) a method for preparing the above described hindered amine compound comprising the step of reacting a compound according to the following formula

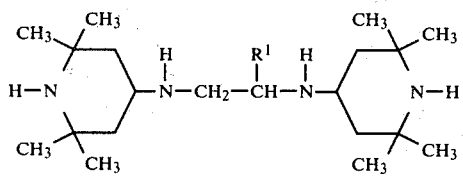

with a compound having the formula

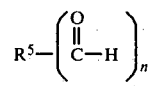

and optionally reacting the resulting product with a compound having the formula R⁴Y wherein
R¹ represents hydrogen or methyl,
R⁴ represents $C_1$ to $C_4$ alkyl, $C_7$ to $C_{18}$ aralkyl or $C_2$ to $C_8$ alkenyl, $R^5$ represents a straight or branched aliphatic, cycloaliphatic or substituted or unsubstituted aromatic group having a valence equal to n, n is 1 or 2 and Y represents halogen.

DESCRIPTION OF INVENTION

There has now been discovered a hindered amine compound, as described herein, which can be used to stabilize organic polymers against light and/or heat induced degradation without many of the disadvantages of prior art compounds used for the same purpose. Advantageously the hindered amine compound described herein in accordance with this invention has low volatility, is essentially non-migrating in an organic polymer and is highly compatible with organic polymers. Low volatility is an important feature especially during the incorporation of the stabilizer compound into the organic polymer and subsequent processing of the organic polymer into finished articles of commerce. Such low volatility reduces or prevents significant odors and contamination of the work place atmosphere as well as reducing or preventing undesirable losses through volatilization of the stabilizer compound during processing. The non-migrating feature is advantageous for obtaining uniform distribution of the stabilizer throughout the organic polymer. High compatibility of the stabilizer with the polymer improves the mixing of the stabilizer into the polymer to achieve a uniform distribution of the stabilizer in the polymer. In addition to being useful as a stabilizer for organic polymers, it is contemplated that the hindered amine compound according to this invention may have such other uses as an insecticide, a fungicide, an anticorrosion agent, a bacteriocide and an antiviral agent.

In accordance with this invention there is provided a hindered amine compound, useful for stabilizing organic polymers against light and/or heat induced degradation, having the following formula

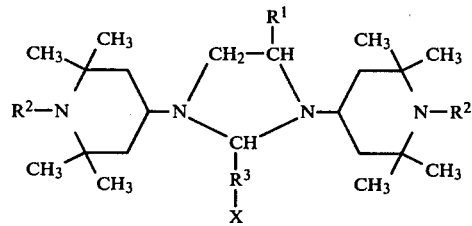 (I)

wherein $R^1$ represents hydrogen or methyl;

$R^2$ represents hydrogen, alkyl having 1 to 8 carbon atoms, alkenyl having 2 to 8 carbon atoms or aralkyl having 7 to 18 carbon atoms;

$R^3$ represents a straight or branched chain alkylene, straight or branched chain alkenylene, unsubstituted or substituted arylene or cycloalkylene group and X represents hydrogen or a group having the following formula

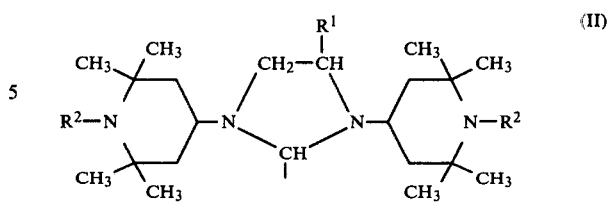 (II)

where $R^1$ and $R^2$ are as previously defined above. Further, there is provided in accordance with this invention an organic polymer composition comprising an organic polymer normally susceptible to light and/or heat induced degradation and a hindered amine compound according to formula (I). In addition, in accordance with this invention there is provided a novel method for making the hindered amine compound according to formula (I) comprising the step of reacting a compound having the following formula

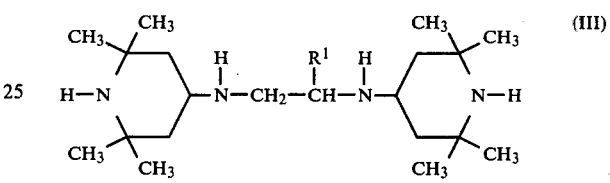 (III)

with a compound having the formula

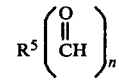

and optionally reacting the resulting product of said reaction with a compound having the formula $R^4Y$ wherein $R^1$ is as defined above for formula (I)

$R^4$ represents alkyl having 1 to 8 carbon atoms, alkenyl having 2 to 8 carbon atoms or aralkyl having 7 to 18 carbon atoms;

$R^5$ represents, when n is 2, a straight or branched chain alkylene, a straight or branched chain alkenylene, an unsubstituted or substituted arylene or cycloalkylene group;

$R^5$ represents when n is 1, a branched or straight chain alkyl, a straight or branched chain alkenyl, an unsubstituted or substituted aryl or a cycloalkyl group;

Y represents bromine, chlorine or iodine and n is 1 or 2

A method for stabilizing an organic polymer is also provided in accordance with this invention comprising the step of adding to an organic polymer, normally susceptible to light and/or heat induced degradation, a hindered amine compound according to formula (I) above. Various embodiments of the hindered amine compound of this invention may be practiced, including, but not limited to, the hindered amine compound according to formula (I) wherein $R^3$ is (1) a straight or branched chain alkylene group, preferably having 1 to 14 carbon atoms, (2) a straight or branched chain alkenylene group, preferably having 2 to 14 carbon atoms and one to three carbon carbon double bonds, (3) a substituted or unsubstituted arylene group preferably alkyl substituted or unsubstituted phenylene or (4) a cycloalkylene group, preferably having six carbon atoms in the ring and wherein (A) $R^1$ is H, $R^2$ is H and X is H; (B) $R^1$ is H, $R^2$ is H and X is according to formula (II); (C) $R^1$ is methyl, $R^2$ is H and X is H; (D) $R^1$ is methyl, $R^2$ is H and X is according to formula (II); (E) $R^1$ is H, $R^2$ is $C_1$ to $C_8$ alkyl (preferably $C_1$ to $C_4$ alkyl) and X is according to formula (II); (G) $R^1$ is methyl, $R^2$ is $C_1$ to $C_8$ (preferably $C_1$ to $C_4$) alkyl and X is H; (H) $R^1$ is methyl, $R^2$ is $C_1$ to $C_8$ (preferably $C_1$ to $C_4$) alkyl and X is according to formula (II); (J) $R^1$ is H, $R^2$ is $C_7$ to $C_{18}$ (preferably $C_7$ to $C_{12}$) aralkyl and X is H; (K) $R^1$ is H, $R^2$ is $C_7$ to $C_{18}$ (preferably $C_7$ to $C_{12}$) aralkyl and X is according to formula (II); (L) $R^1$ is methyl, $R^2$ is $C_7$ to $C_{18}$ (preferably $C_7$ to $C_{12}$) aralky and X is H; (M) $R^1$ is methyl, $R^2$ is $C_7$ to $C_{18}$ (preferably $C_7$ to $C_{12}$) aralkyl and X is according to formula (II); (N) $R^1$ is H, $R^2$ is $C_2$ to $C_8$ (preferably $C_2$ to $C_6$) alkenyl and X is H; (P) $R^1$ is H, $R^2$ is $C_2$ to $C_8$ (preferably $C_2$ to $C_6$) alkenyl and X is according to formula (II); (Q) $R^1$ is methyl, $R^2$ is $C_2$ to $C_8$ (preferably $C_2$ to $C_6$) alkenyl and X is H or (S) $R^1$ is methyl, $R^2$ is $C_2$ to $C_8$ (preferably $C_2$ to $C_6$) alkenyl and X is according to formula (II).

Preferably the hindered amine compound according to this invention is a hindered amine compound according to formula (I) wherein $R^1$ is hydrogen, $R^2$ is hydrogen, methyl or benzyl, $R^3$ is a $C_2$ to $C_{12}$ straight or branched chain alkylene group or phenylene group and X is hydrogen or a group according to formula (II). Most preferably, the compound of this invention is a compound according to formula (I) wherein $R^1$ is hydrogen, $R^2$ is hydrogen, $R^3$ is a $C_2$ to $C_{12}$ straight or branched chain alkylene group or phenylene group and X is hydrogen or a group according to formula (II). When $R^2$ is $C_1$ to $C_8$ alkyl the alkyl group can be a straight or branched chain alkyl group having from 1 to 8, preferably 1 to 4, carbon atoms. Such an alkyl group can, for example, be a methyl, ethyl, propyl, isopropyl, butyl, tertiary butyl, hexyl or 2 ethyl hexyl group. The $R^2$ may be a $C_7$ to $C_{18}$, preferably $C_7$ to $C_{12}$, aralkyl group. Such aralkyl group may be unsubstituted or have up to 3 substituents, preferably alkyl or alkoxy substituents having 1 to 4 carbon atoms, on the aryl moiety. Examples of such an aralkyl group include benzyl, phenethyl, phenbutyl, phenisopropyl, o-methylbenzyl, m-methylbenzyl, p-methylbenzyl, p-tertiary butylbenzyl, 3,5-dimethylbenzyl and methoxybenzyl. When $R^2$ represents a $C_2$ to $C_8$, preferably $C_2$ to $C_6$, alkenyl group the alkenyl group may be a straight or branched chain alkenyl group having 1 to 2, preferably 1, carbon carbon double bond. For example, such an alkenyl group includes vinyl, allyl, methallyl, 1-butenyl, 1-pentenyl, 1-hexenyl, 3-hexenyl and 1,3 pentadienyl.

In one aspect of the hindered amine compound of this invention according to fomula (I) $R^3$ can be a straight or branched chain alkylene group, preferably having from 1 to 14 carbon atoms. Such alkylene groups, for example, include but are not limited to ethylene, propylene, tetramethylene, hexamethylene, octamethylene, decamethylene, tetradecamethylene, ethylethylene, 4-propyl-1,5-pentylene and 2-ethyl-1,6-hexylene. In another aspect of the hindered amine compound of this invention according to formula (I) $R^3$ can be a straight or branched chain alkenylene, preferably having 2 to 14 carbon atoms and from 1 to 3 (more preferably 1), carbon carbon double bond, for example, vinylene, 4-propyl-2-pentenylene, 2-butenylene and 2-methyl-4-hexenylene. In accordance with formula (I) $R^3$ can be a substituted or unsubstituted arylene group. Such arylene group is preferably an unsubstituted arylene having a six carbon atom ring (e.g. 1,4-phenylene, 1,3-phenylene and 1,2-phenylene). However, other arylene groups having a 5 carbon atom ring or a 7 carbon atom ring may also be used as $R^3$ in the practice of the hindered amine compound of this invention according to formula (I). When $R^3$ is a cycloalkylene group such group preferably contains 5 to 7, more preferably 6, carbon atoms in the cycloalkylene ring (e.g. 1,4-cyclohexylene). In the context of the hindered amine compound of this invention according to formula (I), the terms alkylene, alkenylene, arylene and cyclohexylene are meant to identify divalent organic radicals.

The hindered amine compound of this invention, more preferably the compound according to formula (I) may be prepared by a novel method which forms a part of this invention. Thus, the hindered amine compound of this invention according to formula (I) may be prepared by a novel method comprising the step of reacting a compound having the formula

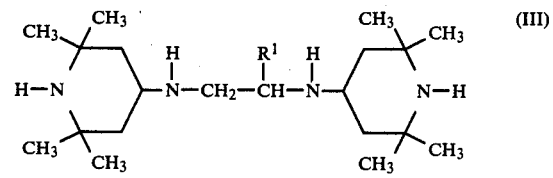

with a compound having the formula

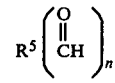

and optionally reacting the resulting product of said reaction with a compound having the formula $R^4Y$ wherein $R^1$, $R^4$, $R^5$, Y and n are as previously defined herein. The compound according to formula III may be prepared by methods known in the art such as, for example, reacting triacetone amine with ethylene diamine and reducing the resulting product in accordance with well known methods. More detailed descriptions of the preparation of the hindered amine compounds of this invention by the novel method forming a part of this invention are given in the examples contained herein. It will be recognized from the description herein that (1) the $R^4$ radical of the compound having the formula $R^4Y$ corresponds to the $R^2$ radical of the compound having formula (I) and (2) and $R^5$ radical of the compound having the formula

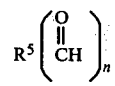

corresponds to the $R^3$ radical of the compound having formula (I). As examples of compounds according to the formula

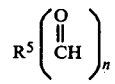

there include, but not limited to, acetaldehyde, butyraldehyde, caproaldehyde, dodecylaldehyde, 2-ethylbutyraldehyde, acrolein, transcinnamaldehyde, 2,4-heptadienal, 2,4-hexadienal, benzaldehyde, methacrolein, phenyl acetaldehyde, 2-phenyl propionaldehyde, p-anisaldehyde, m-anisaldehyde, 2,4-dimethyl benzaldehyde, 2,3-dimethylbenzaldehyde, 2,4-dimethoxybenzaldehyde, isophthaldehyde, mesitaldehyde, o-phthalicdicarboxaldehyde, terephthalicdicarboxaldehyde and glutaraldehyde. Compounds according to the formula $R^4Y$, for example, include but are not limited to methyl chloride, ethyl bromide, hexyl iodide, octyl chloride, allyl chloride, 1-bromo-1-propene, benzyl chloride and (2-chloroethyl)benzene.

There is provided in accordance with this invention a polymer composition having improved resistance to deterioration, induced by light, by heat or by a combination of light and heat, comprising an organic polymer normally susceptible to deterioration induced by light, by heat or a combination of light and heat and a stabilizingly effective amount of a compound having one to two bis(2,2,6,6-tetra-methyl-4-piperidyl) substituted heterocyclic rings in which said heterocyclic ring has five ring atoms, two of which are non-adjacent nitrogen atoms and three of which are carbon atoms and having a 2,2,6,6-tetramethyl-4-piperidyl group bonded to each nitrogen atom of the heterocyclic ring. Further, in accordance with this invention there is provided an organic polymer composition comprising an organic polymer normally susceptible to deterioration induced by light, by heat or by a combination of light and heat and a stabilizingly effective amount of a hindered amine compound according to formula (I).

As organic polymers, normally susceptible to deterioration induced by light, by heat or by a combination of light and heat, usable in the practice of this invention, there are included both natural and synthetic organic polymers. These natural and synthetic organic polymers, for example, include but not limited to (a) homopolymers and copolymers of hydrocarbon monomers having one or two olefinic double bonds (e.g. polyethylene, polypropylene, polybutene-1, polyisobutene, polymethylbutene-1, polymethylpentene-1, polyisoprene, polybutadiene, polystyrene, acrylonitrile-butadiene-styrene terpolymer, ethylene-propylene copolymers, propylene-butene-1 copolymers, ethylene-butene-1 copolymers, propylene-isobutene copolymers and styrene-butadiene copolymers), (b) terpolymers (e.g. terpolymers of ethylene and propylene with diene monomers such as, for example, cyclopentadiene, ethylidenenorborene, hexadiene and pentadiene-1,4) (c) polymerized acrylates and methacrylates (e.g. polymethyl acrylate, polymethyl methacrylate, polybutyl acrylate, polyhexyl acrylate and butyl acrylate-methyl methacrylate copolymer), (d) derivatives of cellulose (e.g. cellulose acetate, cellulose butyrate, cellulose acetate propionate and cellulose acetate butyrate), (d) polyurethanes, (e) vinyl halide homopolymers, vinyl halide copolymers and polymer blends containing vinyl halide homopolymers or vinyl halide copolymers usable in the practice of this invention there, for example, may be used (1) polyvinyl chloride, polyvinylidene chloride, polyvinyl bromide, polyvinyl fluoride, polyvinylidene fluoride, (2) copolymers of vinyl chloride with a copolymerizable ethylenically unsaturated monomer such as vinylidene chloride, vinyl acetate, vinyl butyrate, vinyl benzoate, diethyl fumarate, diethyl matleate, other alkyl fumarates and maleates, vinyl propionate, methyl acrylate, 2-ethylhexyl acrylate, butyl acrylate, ethyl acrylate, and other alkyl acrylates, methyl methacryate, ethyl methacrylate, butyl methacrylate, hydroxyethyl methacrylate and alkyl methacrylate, methyl alpha chloracrylate, styrene, vinyl ethers such as vinyl ethyl ether, vinyl chloroethyl ether, vinyl phenyl ether, vinyl ketones such as vinyl methyl ketone, vinyl phenyl ketone, 1 fluoro-1-chloroethylene, acrylonitrile, chloroacrylonitrile, allylidene diacetate, chloroallylidene diacetate, ethylene and propylene, and (3) polymer blends such as blends of polyvinylchloride and polyethylene, polyvinyl chloride and chlorinated polyethylene, polyvinyl chloride and polymethyl methacrylate, polyvinyl chloride and polybutyl methacrylate, polyvinyl chloride and polystyrene, polystyrene, polyvinyl chloride and acrylontrille-butadiene-styrene copolymer and polyvinyl chloride and polyethylene and polymethyl methacrylate, (f) polymerized non-halogenated vinyl compounds (e.g. polymerized vinyl acetate, vinyl propionate, vinyl butyrate, vinyl benzoate and copolymerized vinylidine compounds such as ethylene-vinyl acetate copolymers, vinyl acetate-vinyl butyrate copolymers and vinyl propionate-vinyl benzoate copolymers) and (g) natural polymers (e.g. cellulose and rubber). Mixtures of organic polymers containing at least one organic polymer normally susceptible to deterioration induced by light, by heat or by a combination of light and heat can be used in the practice of the organic polymer compositions of this invention.

Preferably in the practice of the organic polymer compositions of this invention there are used synthetic organic polymers normally susceptible to deterioration induced by light, by heat or by a combination of light and heat. More preferably there are used homopolymers and copolymers of olefincally unsaturated monomers and mixtures containing said homopolymers and copolymers. Most preferably there are used homopolymers and copolymers of ethylene and propylene and mixtures containing said homopolymers and copolymers.

In one particular aspect the organic polymer composition of this invention comprises a synthetic organic polymer normally susceptible to deterioration induced by light, by heat or by a combination of light and heat and a stabilizingly effective amount of a hindered amine compound according to formula (I), more particularly a hindered amine compound according to formula (I) wherein $R^1$ is hydrogen, $R^2$ is hydrogen, methyl or benzyl, $R^3$ is a $C_2$ to $C_{12}$ straight or branched chain alkylene group or a phenylene group and X is hydrogen or a group according to formula (II), most preferably a hindered amine compound according to formula (I) wherein $R^1$ is hydrogen, $R^2$ is hydrogen, $R^3$ is a $C_2$ to $C_{12}$ straight or branched chain alkylene group or a phenylene group and X is hydrogen or a group according to formula (II). Another aspect of the organic polymer composition of this invention provides an organic polymer composition comprising a homopolymer or copolymer of an olefinically unsaturated monomer, more particularly ethylene and propylene, or a polymer mixture containing said homopolymer or copolymer and a stabilizingly effective amount of a hindered amine compound according to formula (I), more particularly a hindered amine compound according to formula (I) wherein $R^1$ is hydrogen, $R^2$ is hydrogen, methyl or benzyl, $R^3$ is a $C_2$ to $C_{12}$ straight or branched chain alkylene group or a phenylene group and X is a hydrogen or a group according to formula (II), most preferably a hindered amine compound according to formula (I) wherein $R^1$ is hydrogen, $R^2$ is hydrogen, $R^3$ is a $C_2$ to $C_{12}$ straight or branched chain alkylene group or a phenylene group and X is hydrogen or a group according to formula (II). A still further aspect of the organic polymer composition of this invention provides an organic polymer composition comprising a homopolymer or copolymer of vinyl halide monomer or a polymer mixture containing a homopolymer or copolymer or a vinyl halide monomer and a stabilizing effective amount of a hindered amine compound according to formula (I), more particularly, a hindered amine compound according to formula (I) wherein $R^1$ is hydrogen, $R^2$ is hydrogen, methyl or benzyl, $R^3$ is a $C_2$ to $C_{12}$ straight or branched chain alkylene group or a phenylene group and X is hydrogen or a group according to formula (II), most preferably a hindered amine compound according to formula (I) wherein $R^1$ is hydrogen, $R^2$ is hydrogen, $R^3$ is a $C_2$ to $C_{12}$ straight or branched chain alkylene group or a phenylene group and X is hydrogen or a group according to formula (II).

In accordance with the preferred practice of the organic polymer composition of this invention there is provided an organic polymer composition comprising an organic polymer selected from the group consisting of a homopolymer and a copolymer of ethylene and propylene and a polymer mixture containing said homopolymer or copolymer and a stabilizingly effective amount of a hindered amine compound according to formula (I) wherein $R^1$ is hydrogen, $R^2$ is hydrogen, $R^3$ is a $C_2$ to $C_{12}$ straight or branched chain alkylene group or a phenylene group and X is hydrogen or a group according to formula (II).

Various organic polymers, normally susceptible to deterioration induced by light, by heat or by a combination of light and heat, can be used in the practice of the organic polymer compositions of this invention. Such various organic polymers can require widely different amounts of the compound having one or two bis(2,2,6,6-tetramethyl-4-piperidyl) substituted heterocyclic rings having five ring atoms, two of which are non-adjacent nitrogen atoms and three of which are carbon atoms and having a 2,2,6,6-tetramethyl-4-piperidyl group bonded to each nitrogen atom of the heterocyclic ring, preferably the hindered amine compound according to formula (I), for obtaining a stabilizing affect and, therefore, the amount of the hindered amine compound or the hindered amine compound according to formula (I) to be used in the practice of the organic polymer composition of this invention can vary over a wide range. In the practice of the organic polymer composition of this invention, the hindered amine compound or the hindered amine compound according to formula (I) can be used in amount of from 0.001% to 10%, preferably 0.01% to 5%, more preferably 0.05% to 3% by weight based on the organic polymer. It is well recognized that there can be used an amount of the hindered amine compound or the hindered amine compound according to formula (I) substantially greater than the amount needed to stabilize the organic polymer, however, such greater amount of the hindered amine compound or the hindered amine compound according to formula (I) is not needed and can even be wasteful and economically undesirable. It is contemplated that in the practice of the organic polymer composition of this invention any and all species of the hindered amine compound or the hindered amine compound according to formula (I) can be used in amounts in accordance with the above teachings.

The novel organic polymer compositions according to this invention may, in addition to the hindered amine compound or the hindered amine compound according to formula (I), contain conventional additives such as, for example, fillers, pigments, plasticizers, dyes, lubricants and stabilizers well known in the art. Among the fillers, such materials as calcined clays, calcium carbonate and talcs can be used. Pigments well known in the art can be used including such materials as titanium dioxide, carbon black and iron oxide. Included among the well known plasticizers which can be used are the phthalates, sebacates, adipates, phosphates and fatty esters having between 16 and 150 carbon atoms. Lubricants well known in the art which may be used include hydrocarbon waxes, stearyl stearate, cetyl palmitate and other ester waxes. Stabilizers which may be used include the well known ortho hydroxybenzophenones, hydroxybenzotriazoles, organotin carboxylates, organotin sulfides and organotin mercaptocarboxylic acid esters. Antioxidants which can be used include, for example, 2,6-di-(t-butyl-)-4-methyl phenol; 2,6-di(t-butyl)-4-decyloxy phenol and 2-t-butyl-4-octadecyloxy phenol.

Methods well known in the art for compounding plastic compositions for subsequent processing by techniques such as injection molding, extrusion and the like may be used for the preparation of the organic polymer compositions of this invention. Such methods include dry blending with conventional mixers such as the well known Henschel blender, blending on a two roll or three roll mill and tumbling. The hindered amine compound or the hindered amine compound according to formula (I) may be added to the organic polymer separately or in combination with one or more conventional additives (e.g. plasticizer, antioxidant and lubricant). Where the hindered amine compound or the hindered amine compound according to formula (I) is a solid, it may for the sake of convenience be added (i.e. dissolved or dispersed) to a liquid carrier and then the resulting combination added to the organic polymer.

The organic polymer composition of this invention may advantageously be used to make articles of commerce such as, for example, seating, storage containers, toys and pipe.

Advantages such as, for example, improved processing stability (i.e. improved resistance to break down and discoloration during processing) and greater durability of the molded article (i.e. greater resistance of the molded article to deterioration upon exposure to light, to heat or a combination of light and heat) are obtained from the organic polymer composition of this invention.

There is now provided in accordance with this invention a novel process for making a compound having one to two bis(2,2,6,6-tetramethyl-4-piperidyl) substituted heterocyclic rings in which said heterocyclic ring has five ring atoms, two of which are non-adjacent nitrogen atoms and three of which are carbon atoms, and having a 2,2,6,6-tetramethyl-4-piperidyl group bonded to each nitrogen atom of the heterocyclic ring comprising the step of reacting a $N,N^1$-bis(2,2,6,6-tetramethyl-4-piperidyl) substituted 1,2-diamine selected from 1,2-ethylene diamine and 1,2-propylene diamine with an aldehyde selected from the group consisting of aliphatic monoaldehyde and dialdehyde, cycloaliphatic monoaldehyde and dialdehyde, aromatic monoaldehyde and dialdehyde, arylaliphatic monoaldehyde and dialdehyde and alkylaromatic monoaldehyde and dialdehyde and optionally reacting the resulting product of said reaction with an organic mono halide selected from the group consisting of an alkyl monohalide, an aralkyl monohalide and an alkenyl monohalide. Further, there is provided in accordance with this invention a novel process for making a hindered amine compound having the formula

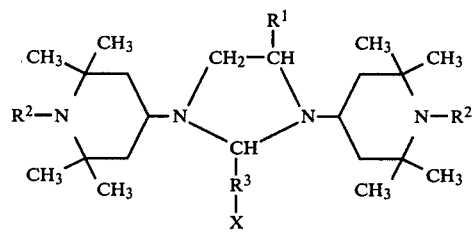

wherein
$R^1$ represents hydrogen or methyl,
$R^2$ represents hydrogen, $C_1$ to $C_8$ alkyl, $C_2$ to $C_8$ alkenyl or $C_7$ to $C_{18}$ aralkyl,
$R^3$ represents a straight or branched chain alkylene group, a straight or branched chain alkenylene group, a substituted or unsubstituted arylene group or a cycloalkylene group and
X represents hydrogen or a group having the formula

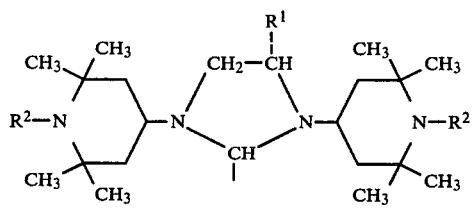

where $R^1$ and $R^2$ are as previously defined above, comprising the step of reacting a compound having the formula

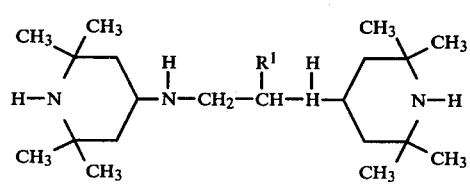

with a compound having the formula

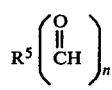

and optionally reacting the resulting product of said reaction with a compound having the formula $R^4Y$ wherein $R^1$ represents hydrogen or methyl, $R^4$ represents a $C_1$ to $C_8$ alkyl group, a $C_2$ to $C_8$ alkenyl group or a $C_7$ to $C_{18}$ aralkyl group, $R^5$ represents, when n is 1, a branched or straight chain alkyl group, a straight or branched chain alkenyl group, a substituted or unsubstituted aryl group or a cycloalkyl group, $R^5$ represents, when n is 2, a straight or branched chain alkylene group, a straight or branched chain alkenylene group, a substituted or unsubstituted arylene group or a cycloalkylene group, Y represents bromine, chlorine or iodine and n is 1 or 2.

In accordance with one embodiment of the process of this invention, the optional step of reacting a compound of having the formula $R^4Y$ with the product of the step of reacting a compound according to formula (III) with a compound having the formula

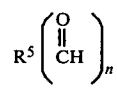

is omitted. As another embodiment of the process of this invention there is provided a method for making a hindered amine compound according to formula (I) comprising the step of reacting a compound according to formula (III), wherein $R^1$ is hydrogen or methyl, with a compound having the formula

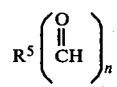

wherein $R^5$ is a straight or branched chain alkyl group or substituted or unsubstituted aryl group (preferably a $C_1$ to $C_{12}$ straight or branched chain alkyl group or phenyl group) and n is 1. A further embodiment of the process of this invention provides a method of making a hindered amine compound according to formula (I) comprising the step of reacting a compound according to formula (III), wherein $R^1$ is hydrogen or methyl, with a compound having the formula

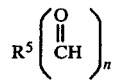

wherein $R^5$ is a straight or branched chain alkylene group or a substituted or unsubstituted arylene group (preferably a $C_2$ to $C_{12}$ straight or branched chain alkylene group or phenylene group) and n is 2. In still another embodiment of the process of this invention there is provided a method for making a hindered amine compound according to formula (I) comprising the step of reacting a compound according to formula (III), wherein $R^1$ is hydrogen or methyl, with a compound having the formula

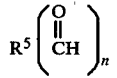

wherein $R^5$ is a straight or branched chain alkyl group or a substituted or unsubstituted aryl group, preferably a $C_1$ to $C_{12}$ straight or branched chain alkyl group or phenyl, and n is 1 and the step of reacting the product of said step with a compound having the formula $R^4Y$ wherein $R^4$ is a $C_1$ to $C_8$ (preferably $C_1$ to $C_4$) alkyl group or a $C_7$ to $C_{18}$ (preferably $C_7$ to $C_9$) aralkyl group and Y is iodine or chlorine (preferably iodine). A still further embodiment of the process of this invention provides a method of making a hindered amine compound according to formula (I) comprising the step of reacting a compound according to formula (III), wherein R[1] is hydrogen or methyl, with a compound having the formula

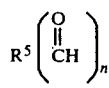

wherein R[5] is a straight or branched chain alkylene group or a substituted or unsubstituted arylene group (preferably a $C_2$ to $C_{12}$ straight or branched chain alkylene group or phenylene group) and n is 2 and the step of reacting the product of said step with a compound having the formula R[4]Y wherein R[4] is a $C_1$ to $C_8$ (preferably $C_1$ to $C_4$) alkyl group or a $C_7$ to $C_{18}$ (preferably $C_7$ to $C_9$) aralkyl group and Y is iodine or chlorine (preferably iodine).

The preferred practice of the process of this invention is a method for preparing a hindered amine compound according to formula (I) comprising the step of reacting a compound according to formula (III) wherein R[1] is hydrogen, with a compound having the formula

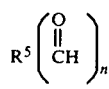

wherein R[5] is, when n is 1, a straight or branched chain alkyl group, preferably having 1 to 12 carbon atoms or a substituted or unsubstituted aryl (preferably phenyl) group, and R[5] is, when n is 2, a straight or branched chain alkylene group preferably having 2 to 12 carbon atoms or a substituted or unsubstituted arylene group, preferably phenylene and n is 1 or 2.

There may be used in the practice of the process of this invention an inert liquid medium, preferably an inert liquid hydrocarbon medium, for carrying out the step of reacting a N,N[1]-bis(2,2,6,6-tetramethyl-4-piperidyl) substituted 1,2-diamine selected from 1,2-ethylene diamine and 1,2-propylene diamine [preferably a compound according to formula (III)] with a monoaldehyde or dialdehyde (preferably a monoaldehyde or dialdehyde having the formula

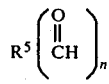

as previously described herein) and optionally reacting the product of said step with a compound having the formula R[4]Y (previously described herein). This inert liquid medium, which preferably is a liquid hydrocarbon, may be a mixture of several organic liquids at least one of which can be non-hydrocarbon organic liquid which is inert to the reactants. Preferably there is at least one liquid hydrocarbon present in such mixture of several organic liquids. Although the use of elevated temperatures is generally preferred in the practice of the process such elevated temperatures will depend upon the nature and composition of the reactants as well as any reaction medium employed. It is, however, desirable to use a temperature high enough to remove by-product water formed during the reaction without decomposing the reactants and/or the hindered amine compound product. A temperature equal to the reflux temperature of the inert liquid medium may be used in the process of this invention provided such reflux temperature is not a temperature causing decomposition of the reactants and/or the hindered amine compound product. Atmospheric pressure or a pressure above or below atmospheric pressure may be used in the practice of the process of this invention. Preferably atmospheric pressure is employed for carrying out the reaction to produce the hindered amine compound product in accordance with this invention.

In the practice of the novel process of this invention there may be used stoichiometric amounts of the reactants or in some circumstances there may advantageously be used amounts of the reactants in excess of the stoichiometric amounts.

The hindered amine compound product of the process of this invention is useful in stabilizing organic polymers (e.g. polyethylene and polypropylene) against deterioration (e.g. deterioration induced by light, by heat or by a combination of light and heat).

The following examples are presented to further describe this invention and the practice thereof and are not intended to be limiting on the invention or its practice. In the following examples all amounts, ratios and percentages are intended to be by weight and the temperatures in degrees Centigrade unless otherwise indicated.

EXAMPLE I

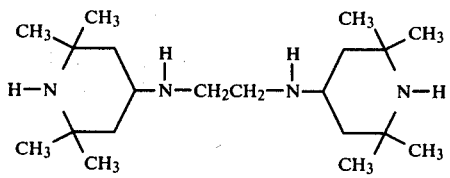

This is an example of the preparation of the above reactant for the preparation of a hindered amine compound of this invention and for the process of this invention.

One mole of triacetone amine and 0.5 moles of ethylene diamine were dissolved in 200 grams of heptane and refluxed into a water trap for 1.0 hour. The heptane was removed by stripping to 110° C. at 15 mm Hg. The residue was dissolved in 300 grams of isopropanol and added to a flask containing 1.0 mole of NaBH$_4$ in 300 grams of isopropanol. After reacting at 40°-45° C. for 10 hours, 200 grams of heptane was added, followed by 500 grams of water. The organic layer was stripped to 130° C. at 15 mm to yield 166.0 grams of crude product. Recrystallization of the product from heptane gave 133.0 grams (72%) of white crystals melting at 67°-70° C. Analysis by GLC indicated 99.3% purity.

EXAMPLE II

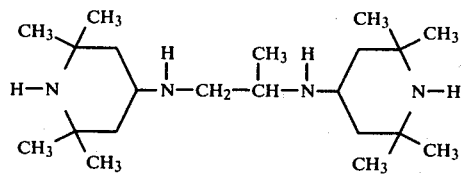

This example shows the preparation of the above reactant for the preparation of a hindered amine compound of this invention and for the process of this invention. The procedure of Example I was followed except that 1,2-diaminopropane was used in place of ethylene diamine.

| Yield | 91.6 grams |
|---|---|
| Appearance | White Crystals |
| Melting Point | 49–51° C. |

EXAMPLE III

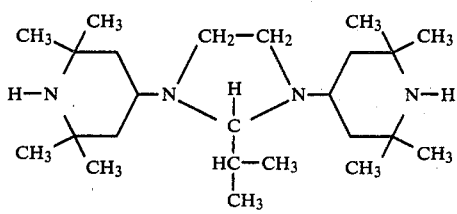

The above compound was prepared in the following manner.

One tenth mole of the compound product of Example I and 0.3 moles of isobutyraldehyde were dissolved in 100 grams of toluene and refluxed into a water trap for two hours. The solvent was removed by stripping to 120° C. at 15 mm and the crude residue recrystallized from 50 grams of heptane.

| Yield | 29.6 grams (75.5%) |
|---|---|
| Melting Point | 92–96° C. |
| Color | White |
| GLC | Shows only one peak |
| IR & NMR | Consistent with the above structure |

EXAMPLE IV

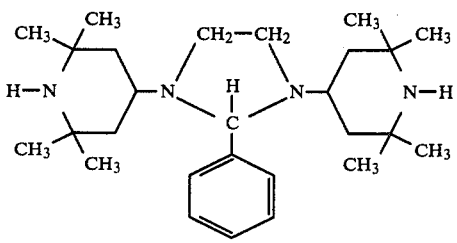

This compound was made by the method of Example III using benzaldehyde in place of isobutyraldehyde.

| Yield | 59.6 grams (93.1%) |
|---|---|
| Melting Point | 87–91° C. |
| GLC | Only one peak |
| IR & NMR | Consistent with the above structure |

EXAMPLE V

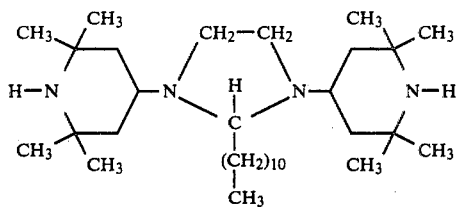

Using the method of Example III with lauryl aldehyde replacing isobutyraldehyde the above compound was obtained in nearly quantitative yield as a yellow oil. IR and NMR analyses were consistent with the above structure.

EXAMPLE VI

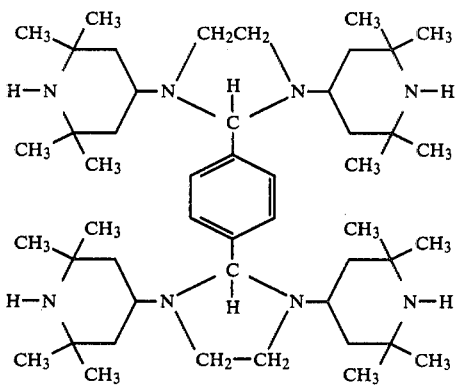

The above compound was prepared in the following manner.

One tenth mole of the compound of Example I and 0.05 mole of terephthalaldehyde in 70 grams of heptane were refluxed for 15 hours into a water trap. The solution was cooled to 20° C. and filtered to remove the product.

| Yield | 37.6 grams (97.1%) |
|---|---|
| Melting Point | 265–270° C. |
| Color | White |
| IR & NMR | Consistent with the above structure |

EXAMPLE VII

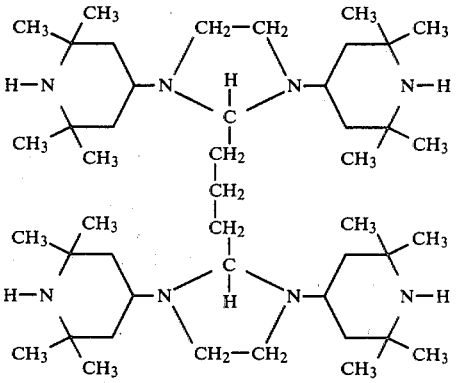

The above compound was prepared in the following manner.

One tenth mole of the compound of Example I and 0.05 mole of glutaraldehyde (49% in water) was mixed with 50.0 grams of xylene and 100 grams of dimethylacetamide. After refluxing into a water trap for 3 hours the solvent was removed by stripping to 130° C./0.5 mm Hg. The crude product was obtained in 97% yield as a yellow glass. IR and NMR on crude product were consistent with the above structure.

EXAMPLE VIII

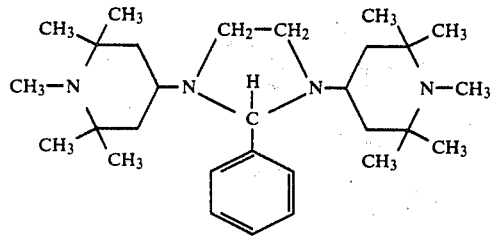

In preparing the above compound the following method was used. The compound of Example IV (0.05 mole) was dissolved in 60 grams of isopropanol and reacted with 0.2 moles methyl iodide at 35°–38° C. for 3 hours. There was added 80 grams of toluene, 100 grams of water and then 0.20 moles of 50% NaOH. The toluene layer was stripped to 120° C. at 15 mm to yield 12.0 grams of crude product as a yellow glass. IR and NMR spectra on the crude product was consistent with the above structure.

EXAMPLE IX

One tenth mole of the compound of Example II was mixed with 0.2 moles of benzaldehyde and 120 grams of toluene. After refluxing into a water trap for 2 hours the solvent was stripped off up to 140° C. at 15 mm. The crude product was recrystallized from hexane.

| Yield | 24.1 grams |
| Color | White |
| Melting Point | 51–56° C. |
| GLC | Only one peak |
| IR & NMR | Consistent with above structure |

EXAMPLE X

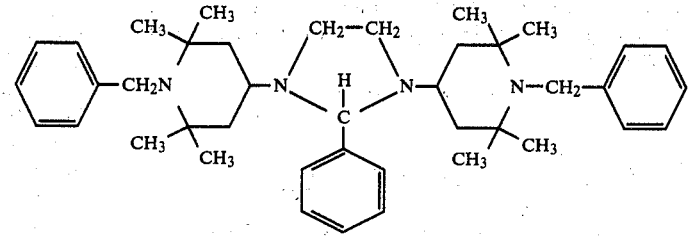

The compound of Example IV (0.05 moles) was dissolved in 80 gms of isopropanol and reacted with 0.3 moles of benzyl chloride at reflux for 18 hours. The reaction mixture was diluted with 100 gms of toluene and treated with 0.3 moles of dilute NaOH. The toluene layer was stripped to 120° C./0.5 mm to yield the crude product as a yellow glass. IR & NMR spectra were in accord with the indicated structure.

EXAMPLE XI

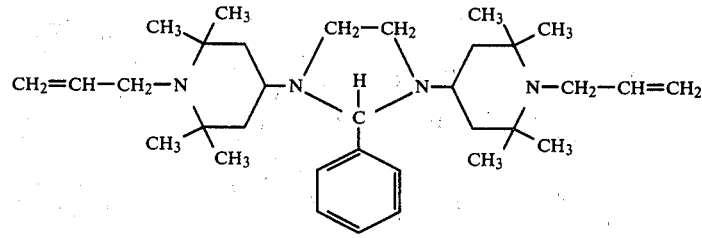

The compound of this example was made by the method of Example X by replacing the benzyl chloride with allyl chloride.

| Yield | 14.0 gms |
| Form | yellow glass |

IR and NMR spectra were consistent with the indicated structure.

EXAMPLE XII

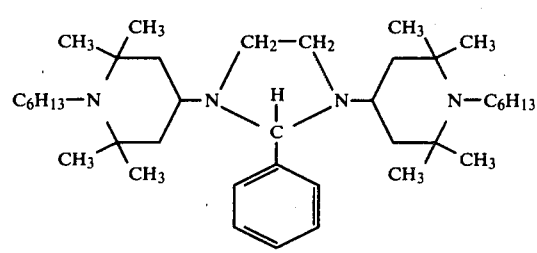

This compound was prepared by the method of Example VIII using n-hexyl iodide in place of methyl iodide. The compound was obtained in good yield as a yellow glass. The NMR spectrum was consistent with the above structure.

EXAMPLE XIII

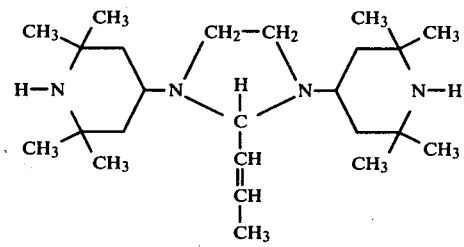

The compound of this example was made by the method of Example III using crotonaldehyde in place of iso-butyraldehyde.

EXAMPLE XIV

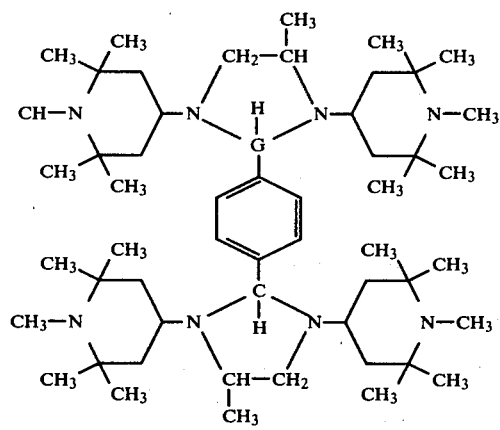

The compound of this example was prepared by the method of Examples VI and VIII using the compound of Example II in place of the compound of Example I.

| Yield | 89.0% |
| --- | --- |
| MP | 211–214° C. |
| Color | White |
| NMR | Consistent with the above structure |

EXAMPLE XV

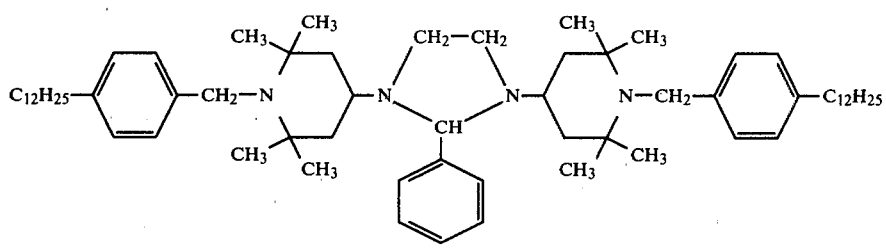

This compound is made by the process of Example X wherein dodecyl benzyl chloride is substituted for the benzyl chloride. IR and NMR spectra were consistent with the above structure.

The ability of the hindered amine compound of this invention to protect organic polymers from degradation by UV light is shown by the following tests.

One hundred parts of polypropylene (Pro-fax ® 5601 obtainable from Hercules, Inc.; Pro-fax ® is a registered trademark of Hercules, Inc.) was mixed with 0.15 parts of calcium stearate (lubricant), 0.10 parts of tetrakis[methylene (3,5-di-terbutyl-4-hydroxyhydrocinnamate)] methane (antioxidant) and 0.5 parts of the various hindered amine compounds of this invention (additive). The mixture was extruded and then pelletized. The pellets were then extruded into fiber (20 denier per filament) and tested for tenacity on an INstron Tensile Tester. The filaments were exposed in a Xenon Arc Weather-Ometer and sampled at regular intervals to determine tenacity. The time required to lose 50% of the original tenacity is a measure of UV stability. The results are shown in Table I.

TABLE I

| | POLYPROPYLENE |
| --- | --- |
| Additive | Hours of Exposure for 50% Loss of Tenacity |
| None | 25 |
| Example I (Prior Art) | 270 |
| Example II (Prior Art) | 255 |
| Example III | 335 |
| Example IV | 330 |
| Example V | 310 |
| Example VI | 320 |
| Example VII | 305 |
| Example VIII | 300 |
| Example IX | 295 |

Tests with high density polyethylene were performed by mixing 100 parts of polyethylene with 0.05 parts of calcium stearate, 0.03 parts of tetrakis[methylene(3,5-di-tertbutyl-4-hydroxyhydrocinnamate)] methane and 0.15 parts of the various hindered amine compounds of this invention (additive). The mixture was milled on a two-roll mill for 5 minutes at 300° F. The milled samples were compression molded at 350° F. for 6 minutes into 20 mil plaques. The plaques were cut into strips and exposed in a Xenon Arc Weather-Ometer. Samples were removed at regular intervals and tested for degradation by a 180° bending test and the results shown in Table II. The test is terminated after 2 consecutive breaks.

TABLE II
HIGH DENSITY POLYETHYLENE

| Additive | Hours to Failure (2 consecutive breaks) |
| --- | --- |
| None | 250 |
| Example I (Prior Art) | 2800 |
| Example II (Prior Art) | 2800 |
| Example III | 3450 |
| Example IV | 3350 |
| Example V | 3300 |
| Example VI | 3400 |
| Example VII | 3350 |
| Example VIII | 3300 |
| Example IX | 3250 |

The hindered amine compounds of this invention were tested in polyvinyl chloride (PVC) by mixing 100 parts of PVC (Geon ®103) a registered trademark of the Goodrich Chemical Company with 0.5 parts of dimethyltin bis-isooctylthioglycolate, 0.5 parts stearic acid and 0.2 parts of the hindered amine compound of this invention (additive). After milling on a two-roll mill at 380° F. for 5 minutes the resin was pressed into 20 mil plaques and exposed in a Xenon Arc Weather-Ometer. Plaque colors were noted after 400 hours of exposure and the results shown in Table III.

TABLE III
POLYVINYL CHLORIDE

| Additive | Plaque Color |
| --- | --- |
| None | Dark Yellow |
| Example I (Prior Art) | Yellow |
| Example II (Prior Art) | Yellow |
| Example III | Pale Yellow |
| Example IV | Pale Yellow |
| Example V | Pale Yellow |
| Example VI | Pale Yellow |
| Example VII | Pale Yellow |
| Example VIII | Pale Yellow |
| Example IX | Pale Yellow |

Polyurethane compositions, prepared from toluene diisocyanate and alkylene polyols, showed much less yellowing when exposed to sunlight if they were protected by the hindered amine compounds of Examples III, VI, or VIII.

What is claimed is:

1. An organic polymer composition comprising an organic polymer normally susceptible to deterioration induced by light, by heat or by a combination of light and heat and a stabilizingly effective amount of a compound having the following formula:

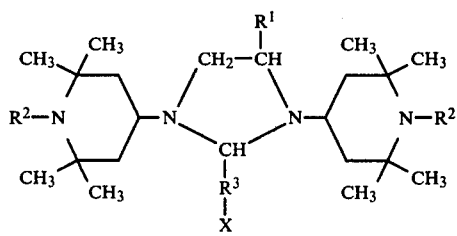

wherein
$R^1$ is hydrogen or methyl;
$R^2$ is hydrogen, alkyl having 1 to 8 carbon atoms, unsubstituted aralkyl having 7 to 18 carbon atoms, or aralkyl having 7 to 18 carbon atoms having up to 3 substituents on the aryl ring selected from alkyl having 1 to 4 carbon atoms and alkoxy having 1 to 4 carbon atoms;
$R^3$ is a straight or branched chain alkylene having 1 to 14 carbon atoms, straight or branched chain alkenylene having 2 to 14 carbon atoms and from 1 to 3 carbon-carbon double bond, unsubstituted arylene having 5 to 7 carbon atoms, or cycloalkylene having 5 to 7 carbon atoms; and
X is a group having the following formula:

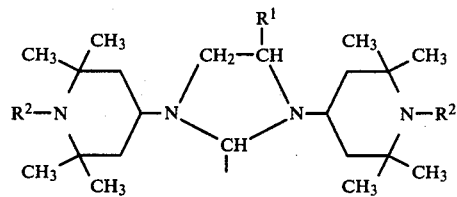

where $R^1$ and $R^2$ are as defined above.

2. An organic polymer composition according to claim 1 wherein the compound is employed in amounts from about 0.001% to about 10% by weight, based on the weight of said polymer.

3. An organic polymer composition according to claim 1 wherein $R^1$ is hydrogen or methyl and $R^2$ is hydrogen or a $C_1$ to $C_8$ alkyl group.

4. An organic polymer composition according to claim 1 wherein $R^1$ is hydrogen or methyl and $R^2$ is a $C_2$ to $C_8$ alkenyl group.

5. An organic polymer composition according to claim 1 wherein $R^1$ is hydrogen or methyl and $R^2$ is unsubstituted aralkyl having 7 to 18 carbon atoms, or aralkyl having 7 to 18 carbon atoms having up to 3 substituents on the aryl ring selected from alkyl having 1 to 4 carbon atoms and alkoxy having 1 to 4 carbon atoms.

6. An organic polymer composition according to claim 1 wherein said polymer is selected from the group consisting of a homopolymer of ethylene or propylene, a copolymer of ethylene, a copolymer of propylene, a polymer mixture having a homopolymer or copolymer of ethylene and a polymer mixture having a homopolymer or copolymer of propylene.

7. An organic polymer composition according to claim 6 wherein $R^1$ is hydrogen.

* * * * *